(12) United States Patent
Vialletel et al.

(10) Patent No.: US 6,205,864 B1
(45) Date of Patent: Mar. 27, 2001

(54) GYRATORY SHEAR PRESS

(75) Inventors: Hugues Vialletel; Sylvain Gallier, both of Angers; Jacky Gaschet, Corne; Francis Moutier, Brains, all of (FR)

(73) Assignee: Laboratoire Central des Ponts et Chayssees, Paris (FR)

( * ) Notice: Subject to any disclaimer, the term of this patent is extended or adjusted under 35 U.S.C. 154(b) by 0 days.

(21) Appl. No.: 09/350,263

(22) Filed: Jul. 11, 1999

(30) Foreign Application Priority Data

Jul. 15, 1998 (FR) .................................................. 98 09036

(51) Int. Cl.[7] ................ G01N 3/08; G01N 3/32
(52) U.S. Cl. ..................... 73/824; 73/813; 73/818
(58) Field of Search ....................... 73/813, 818, 821, 73/822, 824, 825

(56) References Cited

U.S. PATENT DOCUMENTS

| 5,275,056 | 1/1994 | Hamilton et al. . |
|---|---|---|
| 5,323,655 | 6/1994 | Eagan et al. . |
| 5,456,118 | * 10/1995 | Hines et al. ............................ 73/818 |
| 5,606,133 | * 2/1997 | Hines et al. ............................ 73/824 |
| 5,817,946 | 10/1998 | Brovold . |
| 5,824,913 | * 10/1998 | Pyle ....................................... 73/818 |
| 5,939,642 | * 8/1999 | King et al. ........................... 713/813 |
| 6,026,692 | * 2/2000 | Brovold ................................ 73/818 |

FOREIGN PATENT DOCUMENTS 911155    11/1962  (GB) .

* cited by examiner

*Primary Examiner*—Max Noori
(74) *Attorney, Agent, or Firm*—Wolf, Greenfield & Sacks, P.C.

(57) ABSTRACT

This invention relates to a gyratory shear press of which the compression means are disposed in the lower part of the chassis and of which the gyration means are provided in the upper part of the chassis which is in the form of a casing. The mould is introduced in the casing via an opening provided in the upper wall of the casing and adapted to be closed by a lid. The gyration means comprise two concentric sleeves separated from the casing and the mould by bearings. The inner sleeve is mounted to oscillate in the outer sleeve and is inclined by means of a vernier.

15 Claims, 6 Drawing Sheets

GYRATORY SHEAR PRESS

FIELD OF THE INVENTION

The present invention relates to a gyratory shear press for compacting samples of compaction materials.

It concerns more especially a press intended for studies of formulation of granular mixtures, for the development of new formulae and for research concerning the process of compacting materials used for road surfacings, in order to determine the behaviour of bituminous mixtures with respect to compaction and that of materials other than those treated with bituminous binding agents.

BACKGROUND OF THE INVENTION

In this type of press, compaction of the material is obtained by kneading, under low static compression, a sample of material contained in a cylindrical mould limited by parallel ends and maintained at constant temperature, to within standardized temperature tolerances.

Kneading by shearing action is provoked by the movement of the axis of the mould which generates a conical surface of revolution with vertex angle $2\alpha$ while the ends remain at all times perpendicular to the axis of the conical surface.

The resultant axial force F applied to the ends of the sample, the temperature of the mould and the angle $\alpha$, are maintained constant for the whole duration of the test. The cross-section and mass of the sample do not vary during the test, but the height reduces continually.

For each sample, the height and the shearing force are measured and memorized as a function of the number of gyrations.

U.S. Pat. No. 5,275,056 and WO 95/22751 disclose gyratory shear presses in which the mould comprises a peripheral ring extending outwardly and maintained between rollers disposed at different levels and driven in rotation about a vertical axis and which ensure tilting of the mould. In these two documents, the means for compressing the material of the sample are arranged above the mould and the latter rests on a fixed table. These arrangements bring about difficulties for replacing a mould containing one sample by a second mould containing another sample, and for making checks on several samples with different parameters, as it is difficult and long to check and change the angle a.

U.S. Pat. No. 5,323,655 discloses a gyratory shear press in which the compression means are likewise arranged above the mould, the latter resting on a rotating table mounted out-of-center on a rotating plate. Here, it is necessary to ensure a relative movement between the lower end of the mould and the rotating table. This is effected by a ceramic disc interposed between the lower end and the rotating table.

In all these documents, the means for compressing the sample contained in the mould are arranged in the upper part of the apparatus, which increases the volume and consequently the mass of the apparatus, and brings about difficulties in positioning the mould before the test and for removing the sample after compaction.

It is an object of the present invention to propose a gyratory shear press which overcomes these drawbacks.

SUMMARY OF THE INVENTION

To that end, the invention relates to a gyratory shear press for compacting samples of compaction materials, comprising:

a chassis a cylindrical mould of axis X adapted to receive a sample interposed between an upper end and a lower end, maintained parallel to each other;

means for compressing the sample, borne by said chassis and adapted to apply a constant effort on one of said ends along an axis Y perpendicular to said ends;

means for inclining axis X of the mould with respect to axis Y;

gyration means adapted to impart a gyratory movement of axis X about axis Y;

means for controlling the compression means and the gyration means; and means for measuring the heights of the sample between the ends and the shearing efforts of the sample as a function of the number of gyrations of axis X.

The invention attains its object in that:

a) the chassis comprises in its upper part a casing whose rigidity is constant over 360° and which presents, in its upper wall, an opening adapted to be closed by a lid intended to serve as bearing for the upper end, and, in its lower wall, an orifice for the passage of a mobile element of the compression means, which is in abutment on the lower end;

b) the gyration means comprise an outer cylindrical sleeve of axis Y mounted to rotate in the casing via bearings, an inner cylindrical sleeve of axis X mounted to rotate about a counter-mould of axis X intended to receive the mould, via bearings, and means for driving the outer cylindrical sleeve in rotation, said drive means being borne by the casing; the inner cylindrical sleeve being disposed inside the outer cylindrical sleeve and being mounted to oscillate thereon so as to be able to pivot about an axis Z perpendicular to axes X and Y and lying substantially in the plane of the upper end;

c) the means for inclining axis X of the mould with respect to axis Y comprise an angle-adjusting system interposed between the outer cylindrical sleeve and the inner cylindrical sleeve and lying in the median plane perpendicular to axis Z.

The following advantageous arrangements are furthermore adopted:

The lower part of the chassis comprises a lower plate, an upper plate on which the casing is fixed, and a plurality of columns parallel to axis Y and connecting the lower plate to the upper plate, the lower plate supporting the compression means.

The compression means comprise an endless screw driven by second drive means and a sheath driven in translation along axis Y by the endless screw, and whose head is in abutment on the lower end, said sheath being guided along axis Y by rollers cooperating with the columns and traversing an opening made in the upper plate with interposition of a bearing bush. A plate with a low coefficient of friction is interposed between the head of the sheath and the lower end. The second drive means comprise an electric servomotor with reduction gear and a displacement encoder.

The angle-adjusting system is provided with a vernier and a door is arranged in the peripheral wall of the casing in order to access the vernier. The means for measuring the shearing efforts comprise a shear sensor placed inside the angle-adjusting system. Electrical supply of the shear sensor and transmission of the data picked up by the sensor are ensured by a rotating collector.

The casing comprises an inductive detector for counting the number of revolutions of the outer cylindrical sleeve.

The press according to the invention advantageously further comprises a mould-handling system, comprising a bracket disposed above the upper wall of the casing and a winch disposed above the lid and supported by the bracket.

BRIEF DESCRIPTION OF THE DRAWINGS

The invention will be more readily understood on reading the following description given by way of example and with reference to the accompanying drawings, in which.

DESCRIPTION OF PREFERRED EMBODIMENT

Figure 1:
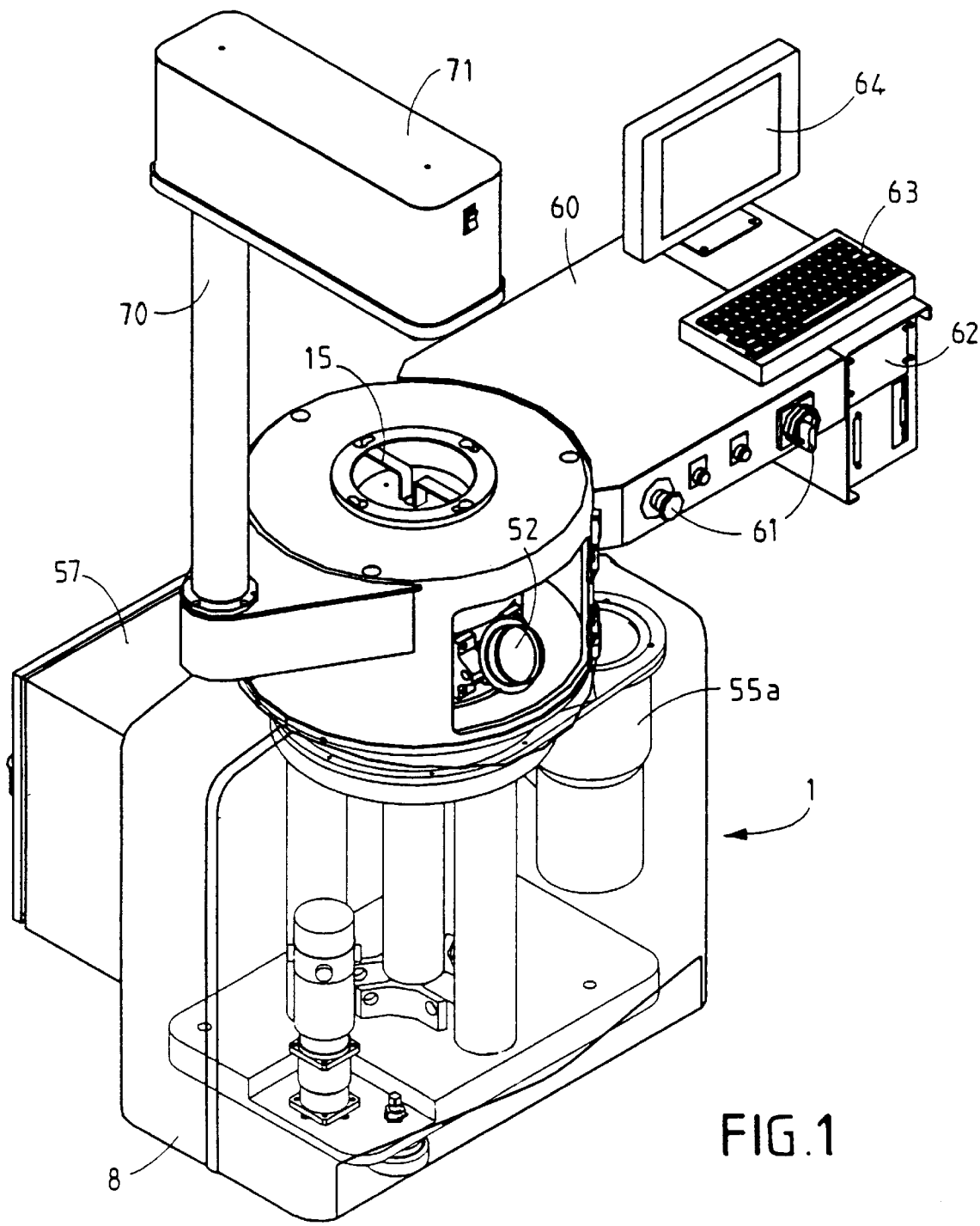
FIG. 1 is a general view in perspective of the gyratory shear press according to the invention.
Figure 2:
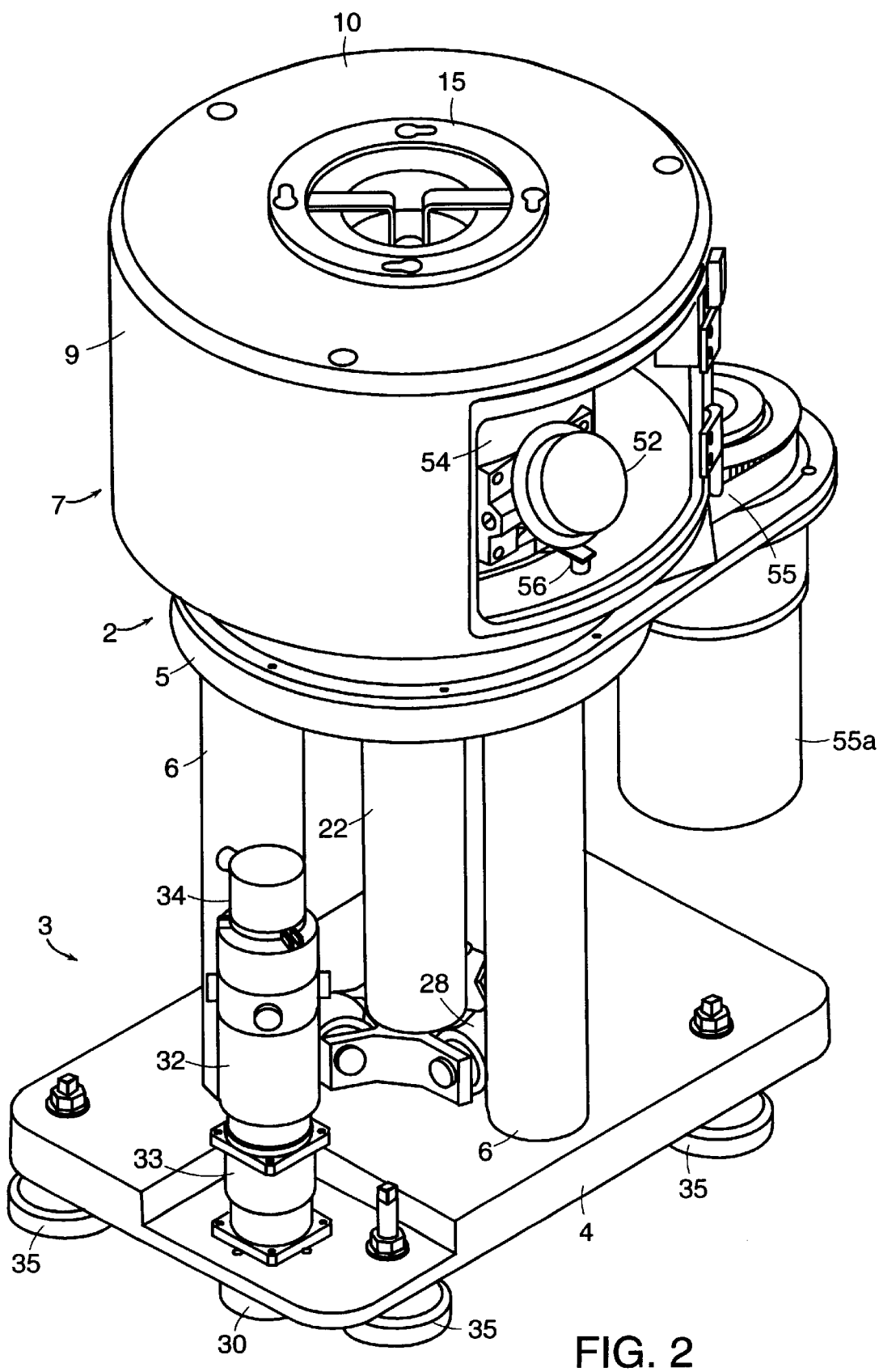
FIG. 2 is an enlarged view of the same machine without the cowling, the switch cabinet, the mould-handling system and the control table.
Figure 3:
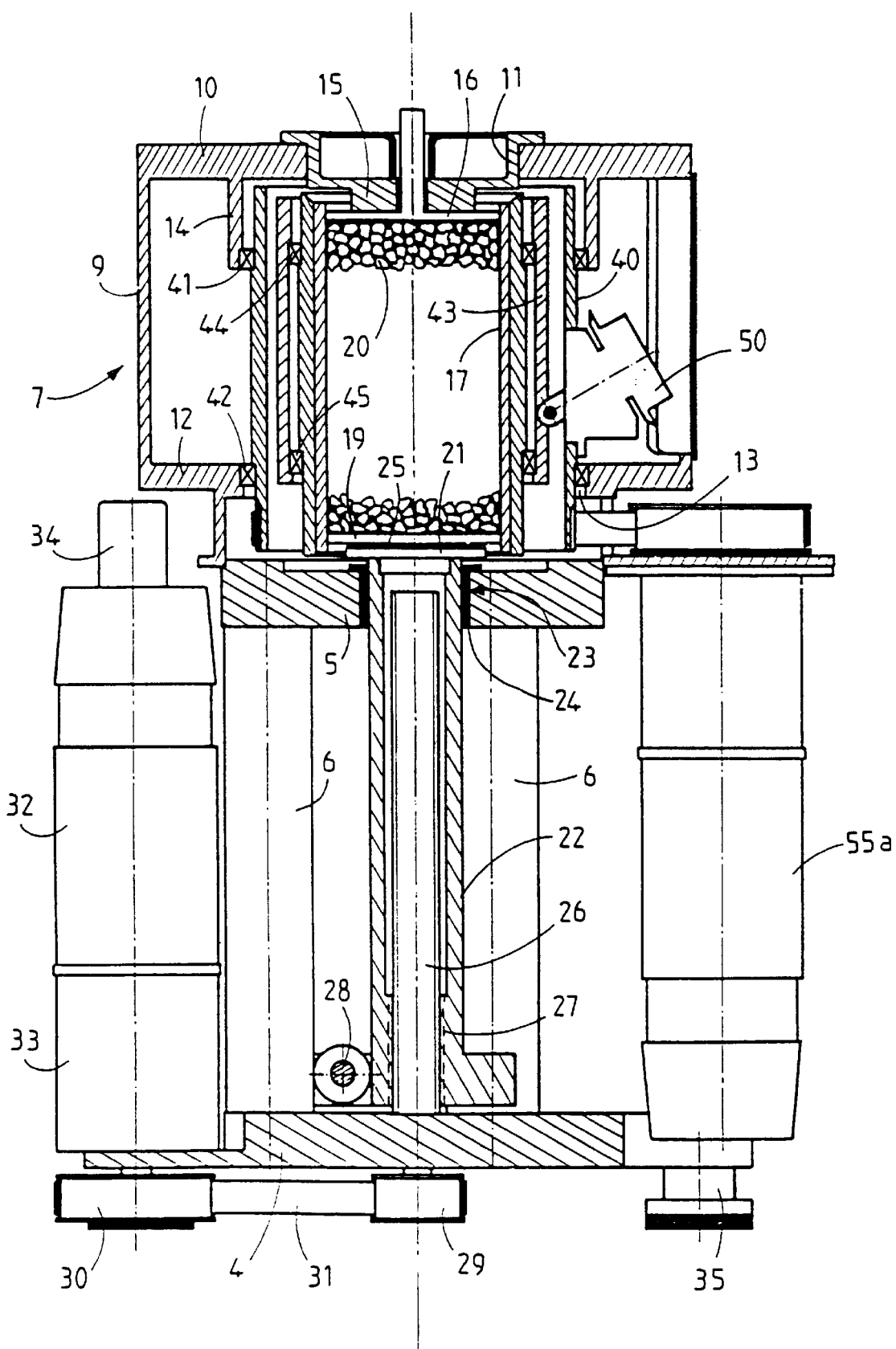
FIG. 3 is a cross-section through the machine along a median vertical plane.
Figure 4:
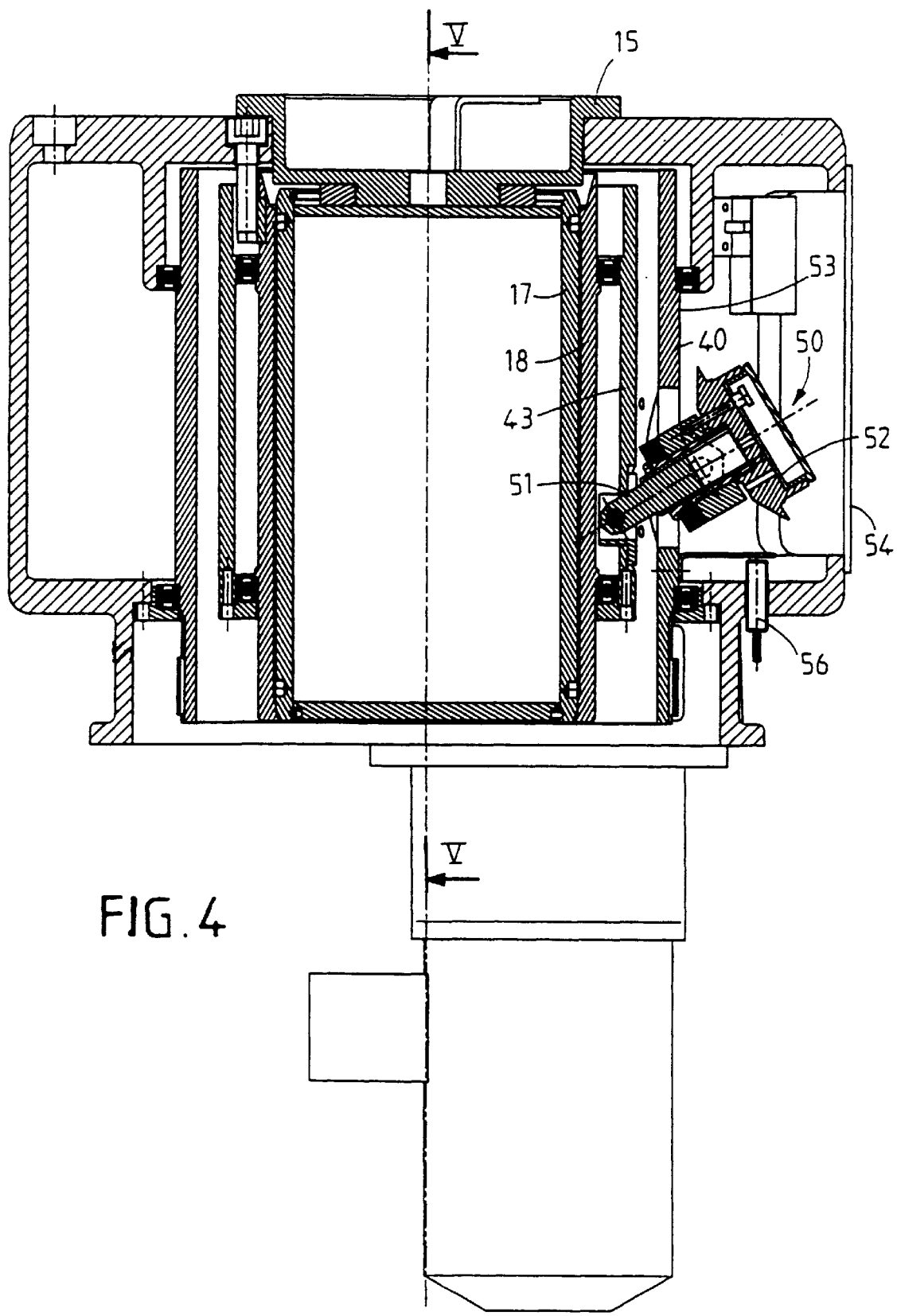
FIG. 4 is a cross-section through the upper part of the machine along a median vertical plane represented by line IV—IV of FIG. 5.

Referring now to the accompanying drawings, the Figures show a gyratory shear press 1 which comprises a chassis 2 whose lower part 3 comprises a lower plate 4 and an upper plate 5 connected by three columns 6 and protected by a cowling 8 and whose upper part 7 is in the form of a hollow rigid casing having a cylindrical peripheral wall 9 of revolution about a vertical axis Y, an upper wall 10 comprising an opening 11 concentric to axis Y and a lower wall 12 fixed on the upper plate 5 and presenting a passage 13 of axis Y. The upper part 7 further comprises a sleeve 14 of axis Y which extends under the upper wall 10 opposite passage 13. The rigidity of casing 7 is constant over 360°.

The opening 11 may be obturated by a lid 15 which serves as bearing for the upper face of an end 16 disposed in the top part of a cylindrical mould 17 of axis X mounted to slide in a cylindrical counter-mould 18. In the bottom part of the mould 17 there is provided a lower end 19 which may slide in the mould 17. The space in the mould 17 defined by the upper end 16 and the lower end 19 is filled with a sample 20 of a compaction material, subjected, on the one hand, to an effort or compression F exerted on the lower end 19 in the vertical direction Y, and, on the other hand, to a gyratory movement of axis X about axis Y.

The effort of compression F is exerted by the head 21 of a sheath 22 of axis Y which passes through an opening 23 of axis Y made in the upper plate 5, with the interposition of a bush 24. A plate 25 made of material with a low coefficient of friction is interposed between the head 21 and the lower face of the lower end 19. The sheath 22 is driven in vertical translation in the direction of axis Y by an endless screw 26 mounted on the lower plate 4 and disposed inside the sheath 22, the latter presenting in its lower part an inner thread 27 cooperating with the outer thread of the endless screw. The sheath 22 is, in addition, guided during its vertical translation by rollers 28 which roll on the outer wall of the columns 6.

The endless screw 26 is driven in rotation, by means of pulleys 29, 30 and a belt 31, by a constant-moment servomotor 32 driving a reduction gear 33 on which the pulley 30 is mounted.

The servomotor 32 is equipped with an angle encoder 34 of which the measurement is representative of the height of the sample 20 contained in the mould 17, between the lower end 19 and the upper end 16. The servomotor 32/reduction gear 33 assembly is disposed above the lower plate 4, while the pulleys 29, 30 and the belt 31 are disposed beneath the lower plate 4, the latter comprising a plurality of stands 35, adjustable in height.

Figure 5:
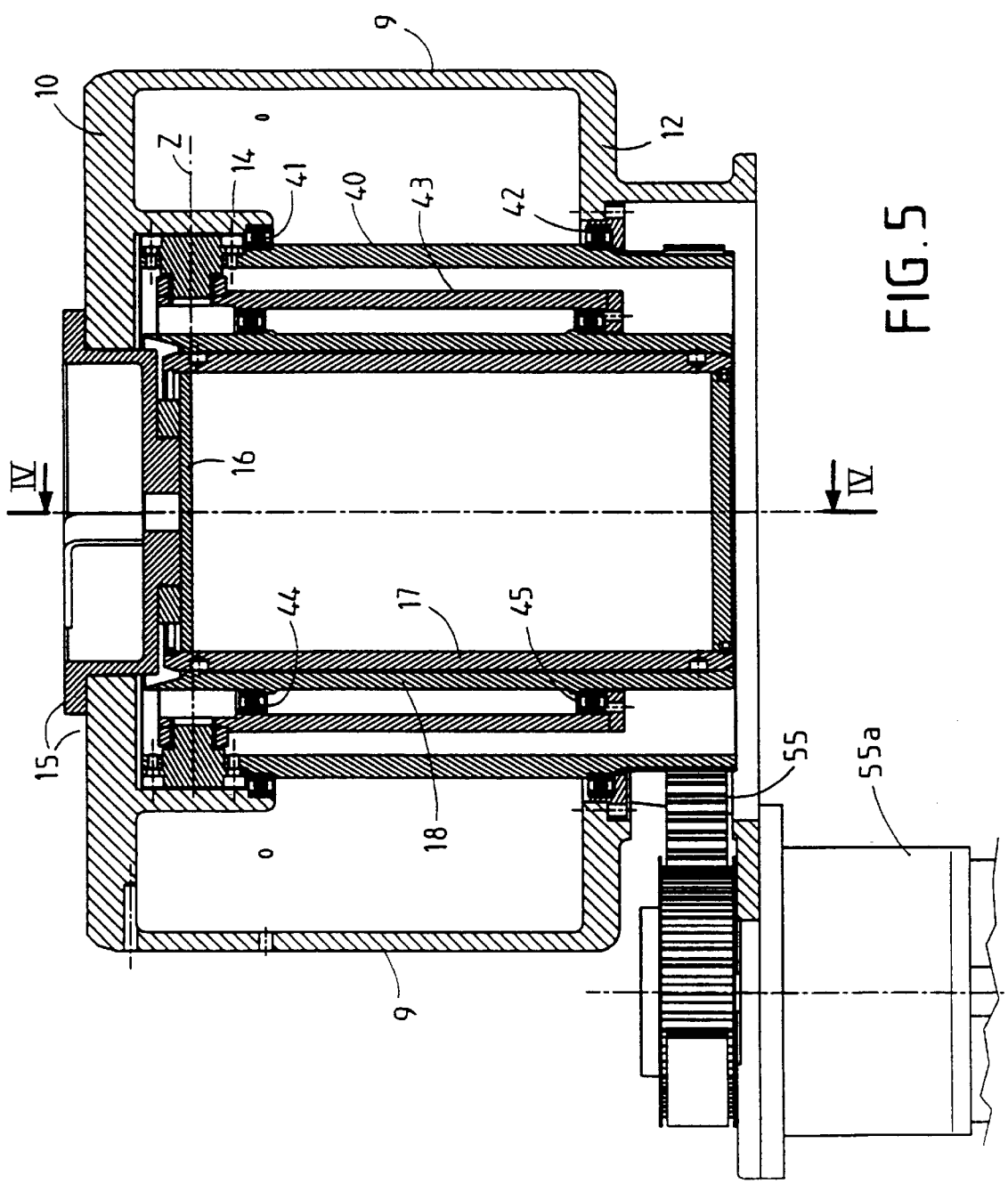
FIG. 5 is a cross-section through the upper part of the machine along a vertical plane represented by line V—V of FIG. 4.
Figure 6:
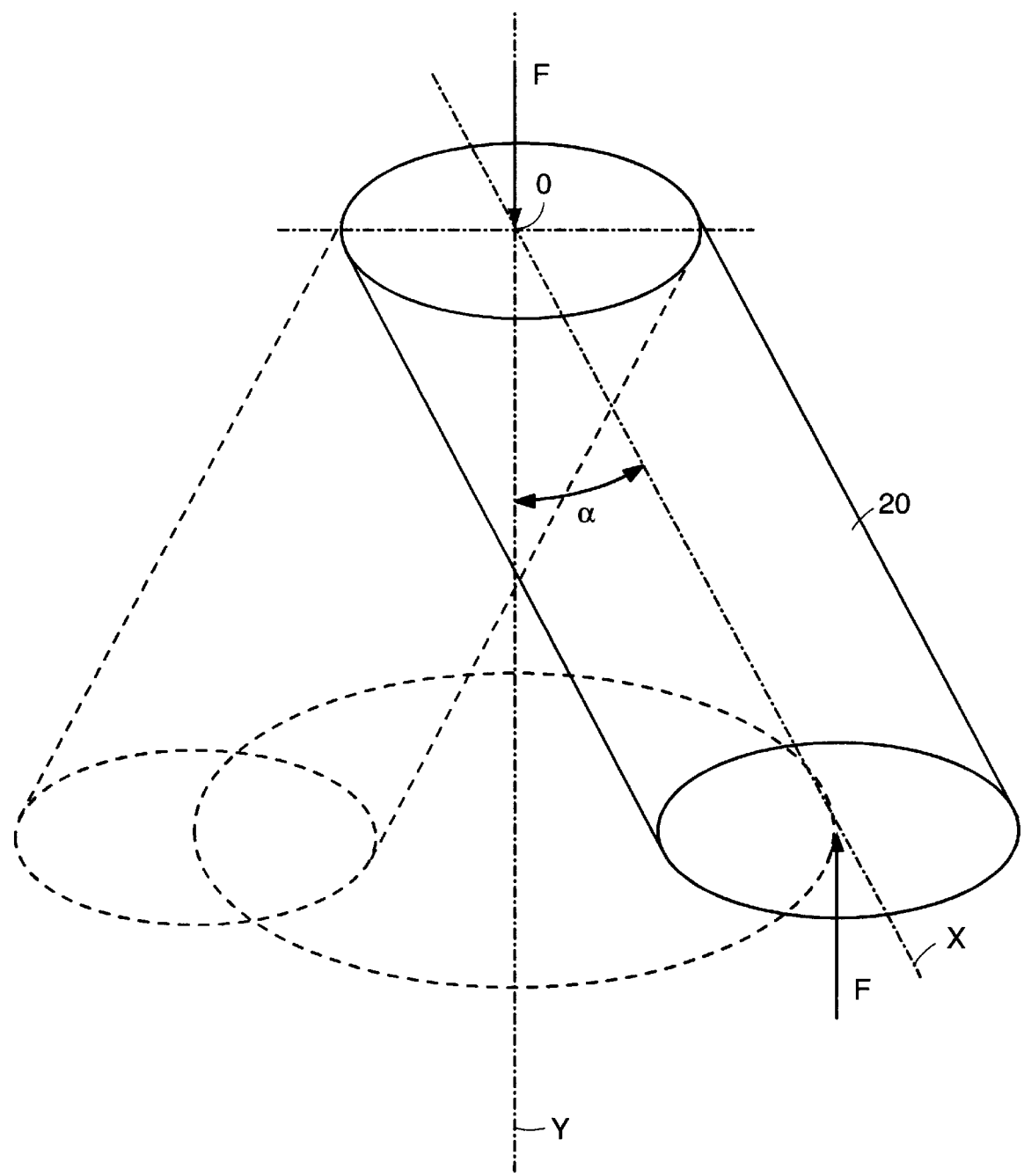
FIG. 6 schematically shows the movement of gyration applied to the sample of material.

The device for gyrating the mould 17 comprises an outer cylindrical sleeve 40 of axis Y mounted to rotate inside the casing 7 by means of a first bearing 41 borne by the sleeve 14 and a second bearing 42 mounted on the periphery of the passage 13 of the lower wall 12, and an inner cylindrical sleeve 43 which is disposed inside the outer sleeve 41 and mounted thereon so as to be able to oscillate about a horizontal axis Z lying substantially in the plane of the lower face of the upper end 16, as shown in FIG. 5.

Two bearings 44 and 45 are interposed between the inner cylindrical sleeve 43 and the counter-mould 18, in order to allow rotation of these two parts with respect to each other, while preventing their relative displacement in the direction of axis X of the mould 17.

A device 50 for adjusting the angle α between the axis X of the mould 17 and the vertical axis Y, is provided in the median vertical plane perpendicular to axis Z. This device 50 is borne by the outer sleeve 40 and cooperates with a screw/nut system 51 fast with the inner sleeve. It comprises a vernier 52 and an effort sensor of which electrical supply and data transmission are ensured by a rotating collector 53.

In order to allow access to the vernier 52 and adjustment of angle α, the peripheral wall 9 of the casing 7 is provided with a door 54 for access.

The outer peripheral sleeve 40 is driven in rotation by an electric motor 55a driving a synchronous belt 55.

The casing 7 is, in addition, equipped with an inductive detector 56 serving to count the number of revolutions of the outer cylindrical sleeve 40.

The vernier 52 allows a setting of the angle α at 0°, which makes it possible to produce test pieces with parallel faces perpendicular to axis X, to effect controls of the apparatus, and a setting of the same angle α from 30' to 2° per step of one minute in a very short time, and without control means.

On the rear of the lower part 3 of the frame 2, there is provided a switch cabinet 57 which ensures electrical supply of the drive motors 32 and 55a and of the different measuring instruments.

To the right of the frame 2 there is fixed, by screws, a panel 60 which comprises the on-off switches 61 of the machine and which supports a microoocomputer 62 controlling the machine. There are connected to the microcomputer 62 a keyboard 63 for introducing the characteristics of the materials to be monitored, a screen 64 for displaying the results of each sample and possibly other accessories, such as mouse, data-storage device, etc. . . . The microcomputer 62 is connected to the angle encoder 34 which furnishes the measurement of the height of the sample to the inductive detector 56 and to the effort sensor placed inside the device for adjusting the angle α, in order to allow storage of the data during gyration of the mould 17 and possibly processing thereof.

To the left of the casing 7 there may be fixed a bracket 70 which supports an electric winch 71 above the lid 15 for handling the mould 17.

The gyratory shear press described hereinabove operates as follows:

A sample 20 of material is disposed in the mould 17 between the two ends 16 and 19.

The mould 17 filled with material is placed in the counter-mould 18 via the upper opening 11, the head 21 of the sheath 22 in that case being in lower position, i.e. slightly above the upper plate 5. The lid 15 is then fixed in the opening 11 by screwing. At the beginning of the series of tests, the demi-vertex angle α of the cone of gyration is displaced by means of the vernier 52. The constant-moment servomotor 32 is switched on, which brings about an increasing vertical effort on the lower end 19 which places the sample 20 in a state of initial compression. When the force of compression attains value F, the motor 55a attains its nominal test speed, and therefore generates rotation of axis X of the mould about axis Y, axis X describing a conical surface of which the vertex 0 lies in the middle of the lower face of the upper end 16. Such gyration provokes shear-kneading of the sample 20. During gyration of the mould 17, the upper end 16 and the lower end 19 remain parallel to each other and perpendicular to the vertical axis Y. For the whole duration of the test, the resultant axial force F applied to the ends of the sample 20 and the angle a are maintained constant within standard tolerances.

What is claimed is:

1. A gyratory shear press for compacting samples of compaction materials, comprising:
    a chassis,
    a cylindrical mould having an X axis and being adapted to receive a sample interposed between an upper end and a lower end, said upper end and said lower end being maintained parallel to each other;
    means for compressing the sample, borne by said chassis and adapted to apply a constant force on one of said ends of said mould along a Y axis perpendicular to said ends;
    means for inclining the X axis of the mould with respect to the Y axis;
    gyration means adapted to impart a gyratory movement of the X axis of the mould about the Y axis;
    means for controlling the compression means and the gyration means; and
    means for measuring a height of the sample between the ends and a shearing force of the sample as a function of a number of gyrations of the X axis;
    the chassis comprising in its upper part a casing whose rigidity is constant over 360° and which presents, in its upper wall, an opening adapted to be closed by a lid intended to serve as a bearing for the upper end of the mould, and, in its lower wall, an orifice for the passage of a mobile element of the compression means, which is in abutment on the lower end of the mould;
    the gyration means comprising an outer cylindrical sleeve having a Y axis and being mounted to rotate in the casing via bearings, an inner cylindrical sleeve having an X axis being mounted to rotate about a counter-mould having an X axis and being intended to receive the mould, via bearings, and means for driving the outer cylindrical sleeve in rotation, said drive means being borne by the casing, the inner cylindrical sleeve being disposed inside the outer cylindrical sleeve and being mounted to oscillate thereon so as to be able to pivot about a Z axis perpendicular to the X and Y axes and lying substantially in the plane of the upper end; and
    the means for inclining the X axis of the mould with respect to the Y axis comprising an angle-adjusting system interposed between the outer cylindrical sleeve and the inner cylindrical sleeve and lying in a median plane perpendicular to the Z axis, the angle adjusting system pivoting the mould about a point disposed substantially in the plane of the upper end of the mould.

2. The press of claim 1, wherein the lower part of the chassis comprises a lower plate, an upper plate on which the casing is fixed, and a plurality of columns parallel to axis Y and connecting the lower plate to the upper plate, the lower plate supporting the compression means.

3. The press of claim 2, wherein the compression means comprise an endless screw driven by second drive means and a sheath driven in translation along axis Y by the endless screw, and whose head is in abutment on the lower end, said sheath being guided along axis Y by rollers cooperating with the columns and traversing an opening made in the upper plate with interposition of a bearing bush.

4. The press of claim 3, wherein a plate with a low coefficient of friction is interposed between the head of the sheath and the lower end.

5. The press of claim 3, wherein the second drive means comprise an electric servomotor with reduction gear and a displacement encoder.

6. The press of claim 1, wherein the angle-adjusting system is provided with a vernier and a door is arranged in the peripheral wall of the casing in order to access the vernier.

7. The press of claim 6, wherein the means for measuring the shearing force comprise a shear sensor placed inside the angle-adjusting system.

8. The press of claim 7, wherein electrical supply of the shear sensor and transmission of the data picked up by the sensor are ensured by a rotating collector.

9. The press of claim 1, wherein the casing comprises an inductive detector for counting the number of revolutions of the outer cylindrical sleeve.

10. The press of claim 1, wherein it further presents a mould-handling system, comprising a bracket disposed above the upper wall of the casing and a winch disposed above the lid and supported by the bracket.

11. A gyratory shear press for compacting samples of compaction materials, comprising:
    a chassis, a lower portion of the chassis comprising a lower plate, an upper plate on which a casing is fixed and a plurality of columns disposed substantially parallel to the Y-axis and connecting the upper plate to the lower plate;
    a cylindrical mould having an X axis and being adapted to receive a sample interposed between an upper end and a lower end, said upper end and said lower end being maintained substantially parallel to one another;
    means disposed on the lower plate for compressing the sample and being adapted to apply a constant force on one of said ends of said mould along a Y axis which is generally perpendicular to said ends, the compression means comprising an endless screw driven by second drive means and a sheath driven in translation along the Y axis by the endless screw, a head of the endless screw being in abutment with the lower end of the mould, said sheath being guided along the Y axis by rollers cooperating with the columns and traversing an opening in the upper plate through a bushing;
    means for inclining the X axis of the mould with respect to the Y axis, the inclining means comprising an angle-adjusting system;
    gyration means adapted to impart a gyratory movement of the X axis of the mould about the Y axis; and means for controlling the compression means and the gyration means.

12. The press of claim 11 wherein a plate with a low coefficient of friction is interposed between a head of the sheath and the lower end of the mould.

13. The press of claim 11 wherein the second drive means comprises an electric servomotor with a reduction gear and a displacement encoder.

14. A gyratory shear press for compacting samples of compaction materials, comprising:

- a cylindrical mould having an X axis and being adapted to receive a sample interposed between an upper end and a lower end, said upper end and lower end being maintained substantially parallel to one another;
- means for compressing the sample and being adapted to apply a constant force on one of said ends of said mould along a Y axis which is generally perpendicular to said ends;
- means for inclining the X axis of the mould with respect to the Y axis, the inclining means comprising an angle adjusting system and a vernier;
- gyration means adapted to impart a gyratory movement of the X axis of the mould about the Y axis;
- means for controlling the compression means and the gyration means; and
- means for measuring a height of a sample between the ends and a shearing force of the sample as a function of a number of gyrations of the X axis, said measuring means comprising a shear sensor disposed inside the angle adjusting system.

15. The press of claim 14 further comprising a rotating collector for supplying electricity to the shear sensor and transmitting data picked up by the shear sensor.

* * * * *